United States Patent [19]

Lederman et al.

[11] 4,180,792
[45] Dec. 25, 1979

[54] TRANSMIT-RECEIVE TRANSDUCER ARRAY AND ULTRASONIC IMAGING SYSTEM

[75] Inventors: Frank L. Lederman; Jerome J. Tiemann, both of Schenectady, N.Y.

[73] Assignee: General Electric Company, Schenectady, N.Y.

[21] Appl. No.: 884,952

[22] Filed: Mar. 9, 1978

[51] Int. Cl.² .............................................. G01S 9/66
[52] U.S. Cl. .......................................... 367/7; 73/626; 343/100 LE; 128/660; 367/122
[58] Field of Search .............. 340/1 R, 5 MP; 73/624, 73/625, 626, 628; 343/100 LE; 128/2 V

[56] References Cited
U.S. PATENT DOCUMENTS

| 3,999,422 | 12/1976 | Lehmann et al. | 73/626 X |
| 4,023,172 | 5/1977 | Schmitt | 343/100 LE X |

OTHER PUBLICATIONS

Endoh et al., *Bull. P.M.E. (T.I.T.)*, No. 37, Mar. 1976, pp. 1-6.
Cottony, *IEEE Trans. on Antennas and Propagation*, vol. AP-18, No. 6, Nov. 1970.

*Primary Examiner*—Richard A. Farley
*Attorney, Agent, or Firm*—Donald R. Campbell; Joseph T. Cohen; Marvin Snyder

[57] ABSTRACT

A linear transducer array with low overall side lobe sensitivity for use in steered beam imagers has a different interelement spacing for transmit than for receive, and preferably has a shorter transmit array with elements spaced at one-half wavelength as the center portion of a longer receive array whose unit elements are spaced at a full wavelength. Two or more elements in the center portion can be coupled together to a receiving channel to maintain constant spacing for the receive aperture in a 100% active transducer.

10 Claims, 8 Drawing Figures

TRANSMIT-RECEIVE TRANSDUCER ARRAY AND ULTRASONIC IMAGING SYSTEM

BACKGROUND OF THE INVENTION

This invention relates to ultrasonic imaging, and more particularly to a transmit-receive transducer array and to a sector scan imaging system incorporating the array.

A steered beam B-scan ultrasonic imaging system based on phased array principles has a linear transducer array as depicted in FIG. 1., and to make a sector scan the elementary transducers are pulsed in time sequence to generate angulated acoustic beams at many angles relative to the normal at the midpoint of the array. Echoes reflected by targets in the direction of a transmitted beam arrive at the transducer elements at different times and are time delayed by different amounts before coherent summation to generate a focused echo signal. A real time cardiac scanner is described by Thurstone and VonRamm in "A New Ultrasonic Imaging Technique Employing Two-Dimensional Electronic Beam Steering", Acoustic Holography, Vol. 5, 1974, Plenum Press, N.Y., pp. 249-259.

The radiation pattern or sensitivity pattern of the transducer array during transmission and reception has, in addition to the main beams, grating side lobes displaced from the main beams at an angle that is dependent upon the spacing between elements. As the interelement spacing decreases the side lobe structure moves farther away from the main beam; overall sensitivity is the product of the transmit and receive array functions. A known phased array has low side lobe levels because the elements, which are used for both transmit and receive, are spaced uniformly at half-wavelength intervals. Resolution and artifact levels, however, are a function of maximum aperture, and to achieve reasonable resolution at the half-wavelength spacing it is necessary to have a large number of elements and transmitting and receiving channels.

The problem to be solved is that when the cost of a system is proportional to the number of transducer elements or channels and when the resolution and artifact levels are a function of maximum aperture, wide transducer spacing gives the best resolution per unit cost. But the side lobe structure moves closer and closer to the main beam and becomes objectionable when the interelement spacing is increased. In this case targets in the direction of the side lobe as well as the main beam may generate echoes which are received and contribute to the focused echo signal. What is wanted is to maintain the cost-effective use of transducers while eliminating degradation of the image caused by unwanted side lobes. Another important consideration for a cardiac scanner is that the physical size of the array should be small because it is placed between or under the ribs when viewing the heart.

SUMMARY OF THE INVENTION

A transmit-receive transducer array with low overall side lobe sensitivity has a different interelement spacing for transmit than for receive while maintaining a constant spacing for both transmit and receive apertures. Then the grating side lobe patterns upon transmission and reception are at substantially different angles from the main beam and the product of side lobe sensitivities is small. The usual configurations have a single row of transducer elements comprised of a shorter transmit array of equally spaced unit transmit elements approximately centered within a longer receive array of equally spaced unit receive elements, the spacing between unit transmit elements being substantially less than the spacing between unit receive elements. This reduces the requirement for many transmitting channels and pulsers and makes possible a wide-aperture array system with good resolution.

A 100% active and physically small transducer according to the preferred embodiment has a central sub-array of transmit-receive elements spaced at one-half wavelength and two end sub-arrays of receive-only elements spaced at a full wavelength. The transmit-receive elements are electrically coupled together by groups of two during reception such that each group functions as a unit receive element with a full wavelength interelement spacing. The connected-together pair of transmit-receive elements feeds received echo signals into a single receiving channel where the combined signal is delayed to focus the echoes. Another embodiment of the transducer array has a center portion comprised of transmit-receive elements alternating with receive-only elements at a half wavelength spacing, and two end portions comprised of receive-only elements at a full wavelength spacing.

The steered beam ultrasonic imager in which the transmit-receive transducer is employed is either a single-sector or a multi-sector scanner with applications in medical examination and the non-destructive testing of metal and ceramic parts.

DESCRIPTION OF THE PREFERRED EMBODIMENTS

Grating side lobe sensitivity patterns are the products of the transmit and receive array functions. The effects of side lobe structures can be suppressed by arranging that the transmit array has a small pattern in the direction of the receiver side lobe and therefore does not transmit appreciable energy in that direction so that the potential targets are not excited. That is, it is possible to escape from the objectionable side lobe structure of the receiver by having the side lobe structure of the transmitter at a different angle, or vice versa. At the system level, it is advantageous for several reasons to have a smaller interelement spacing on transmit than on receive. A particularly convenient choice is to have a smaller transmit array with elements spaced at one-half wavelength serving as the center portion of a larger receiver array whose elements or unit elements are spaced at a full wavelength.

Figure 1:
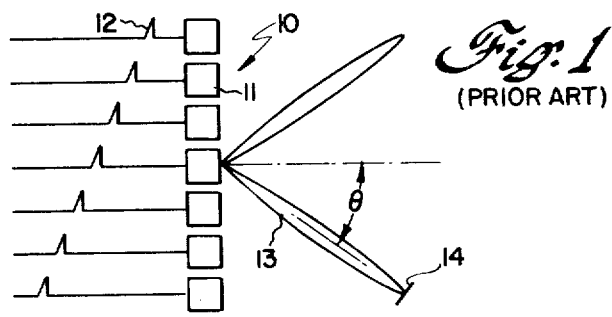
FIG. 1 is a sketch illustrating operation of a prior art single-sector steered beam ultrasonic imager.

Before proceeding the operation of a prior art single sector steered beam ultrasonic imager will be reviewed with reference to FIG. 1. Linear transducer array 10 according to conventional practice has equally spaced elementary transducers 11 serving at both transmit elements and receiver elements. The transducer elements are energized by excitation pulses 12 in a linear time sequence to form an ultrasound beam 13 and direct the beam in a preselected azimuth direction to transmit a pulse of ultrasound. In order to steer the beam electronically to an angle $\theta$ degrees from the normal to the array longitudinal axis, a time delay increment $T_i = (i-1)d \sin \theta$ is added successively to each ith signal as one moves down the array from one end ($i=1$) to the other ($i=N$) to exactly compensate for the propagation path time delay differences that exist under plane wave (Fraunhofer) conditions. By progressively changing the time delay between successive excition pulses, the angle $\theta$ at one side of the normal is changed by increments, and to form a steered beam at the other side of the normal the timing of excitation pulses 12 is reversed so that the bottom transducer in FIG. 1 is energized first and the top transducer is energized last. The total sector scan angle is approximately 60° to 90°. Echoes returning from targets 14 in the direction of the transmitted main beam arrive at the transducer elements at different times necessitating relative delaying of the received echo electrical signals by different amounts so that all the signals from a given point target are summed simultaneously by all elements of the array. The magnitudes of the time delays of the individual echo signals are the same as during the transmission operation to compensate for acoustic path propagation delay differences, and these are referred to as beam steering time delays, or simply steering delays. In B-scan imaging focusing is not essential but improves image quality by increasing resolution and reducing some kinds of artifact problems. Electronic focusing, like beam steering, is accomplished by the use of channel-to-channel electronic signal delay differences to compensate for propagation path time delay differences from the focal point to the various individual array element positions. The beam steering and focusing time delays are additive, i.e., if one applies the time delay set required to steer the beam to an angle $\theta$ and then adds the time delay set required to focus at a range R, the focal point will be located at range R measured along an axis $\theta$ degrees from the normal. The receiving focus can be dynamically changed to track the range from which echoes are being received during the echo reception period by a one step or multi-step approximation.

To effect coherent information of the contributions from all the receive elements and receiving channels, one per transducer element, the delayed echo signals from the multiple receiving channels are fed to a summing amplifier at the output of which is a focused echo signal or raw video data. This is further explained in detail in the discussion of FIG. 8. The focused echo signal, with or without post processing to improve the image quality and to convert the sector scan format to raster format, controls the electron beam intensity of a cathode ray tube or television monitor as the image is built up scan line by scan line. A real time imaging system for cardiology requires a frame rate of about 30 frames per second to prevent blurring of the portion of the heart being pictured on the television screen.

The instant transmit-receive transducer array for steered beam ultrasonic imagers as more broadly defined has a single row of electroacoustic transducer elements comprised of a transmit array of equally spaced unit transmit elements and a receiver array of equally spaced unit receive elements, the interelement spacing of the unit transmit elements and unit receive elements being substantially different. The two values of interelement spacing are chosen such that the grating side lobe upon transmission is at a substantially different angle from the main beam than is the grating side lobe upon reception and the product of side lobe sensitivities is small. Ordinarily, the interelement spacing of the unit transmit elements is less than the interelement spacing of the unit receive elements, but the converse is possible. The transmit and receive arrays with different spacings are interleaved with one another and the total transducer is physically small. It would be possible to have two separate arrays with different spacings mounted side by side, but this results in a bigger and less maneuverable transducer probe, and moreover the two arrays are not colinear and do not have maximum sensitivity. For cardiology, a small, compact transducer probe is necessary because the heart is viewed from between the ribs or can be placed beneath the bottom rib.

Figure 2:
FIG. 2 is a diagram of a transmit-receive array with a relatively small transmit array spaced at one-half wavelength at the center of a receive array whose elements are spaced at a full wavelength.

One embodiment of the transmit-receive transducer array depicted diagrammatically in FIG. 2 has a shorter transmit array of equally spaced transmit elements that is centered or approximately centered within a longer receive array of equally spaced receive elements. Receive-only elements are designated as R, transmit-receive elements as TR, and transmit-only elements as T, and are typically made of piezoelectric material. The interelement spacing of the transmit elements is one-half wavelength of the transmitted ultrasonic energy, and the interelement spacing of the receive elements is a full wavelength, but other values can be used. This configuration is cost effective and has a wide receive aperture for good resolution, and further minimizes the artifact side lobe levels of the system. Since dynamic focusing is possible in the receive mode, the receiver aperture is not limited by the depth of field of the focusing lens and it is therefore desirable to use as wide an aperture as possible for best resolution. The transmit aperture, on the other hand, is limited to the first half Fresnel zone at the nearest point in the field of view, and this insures that each of the transmitted beams arrives at the target with approximately the same phase. In this configuration, the receive and transmit arrays each have constant spacings for ease of implementation of steering and focusing. Steering to wide angles requires that the transducers have wide acceptance angles, thereby requiring narrow element width. The separate transmit elements and receive elements are all unit elements and each is associated with an individual transmitting channel or receiving channel. There are fewer transmit elements than receive elements and this approach has the advantage of minimizing cost by eliminating the need for many expensive pulser circuits. There are also fewer receiving channels than would be the case if the same maximum aperture were achieved by more receive elements at narrower spacings.

Figure 3:
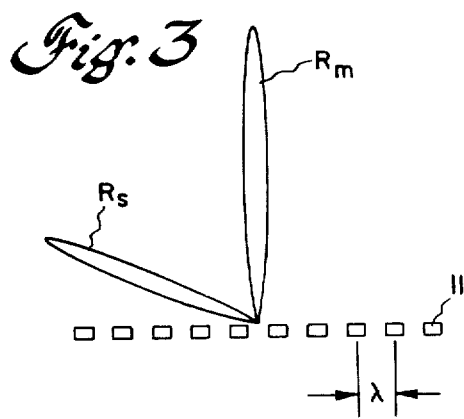
FIGS. 3-5 show the main and side lobe structure for prior art transducer arrays with equally spaced elements.
Figure 4:
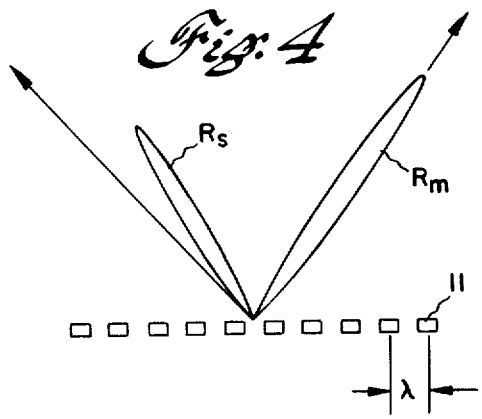
Figure 5:
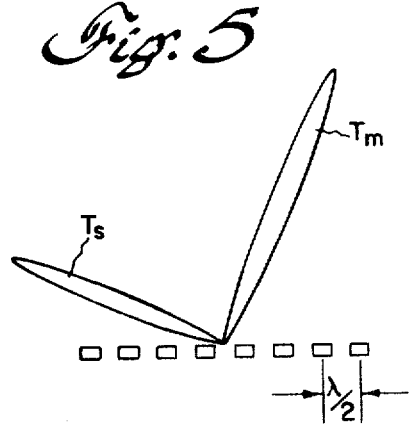
Figure 6:
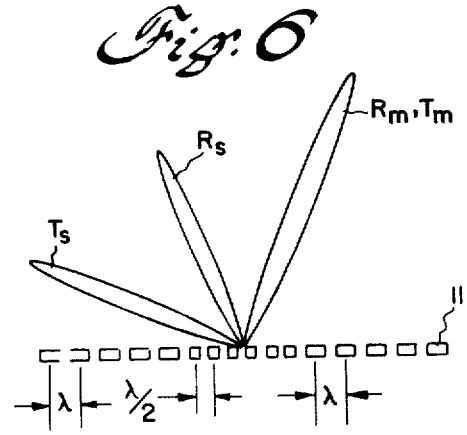
FIG. 6 shows the main and side lobe structure for the transmit-receive transducer arrays of the invention.

The receive array with a spacing between elements of one wavelength has a grating side lobe structure close enough to the main beam that it becomes particularly objectionable when steering at wide angles because the side lobe is then within the viewing field. However, the transmitter array with a smaller spacing between elements has a very small pattern in the direction of the receiver side lobe and does not transmit appreciable energy in that direction so that potential targets are not excited. The transmitter side lobe is at a much greater angle from its main beam than is the receiver side lobe from its main beam. Since the overall side lobe structure of the system is the product of the grating side lobe pattern of the transmitting array multiplied by that for the receive array, the use of different interelement spacings greatly reduces the level of the resulting pattern. In FIG. 3, the sensitivity pattern with a main beam $R_m$, a grating side lobe $R_s$, and several very small diffraction side lobes (not shown) is illustrated for an array of receive elements 11 with a constant one wavelength spacing. Here the transmitted beam is approximately normal to the array. As the transmitted beam is steered to other angles while making the sector scan, the steering delays in the receiving channels are changed correspondingly. In FIG. 4 the receiver main beam and grating side lobe are rotated upon steering to wide angles such that the grating side lobe structure $R_s$ is within the acceptance angle of the transducers indicated by two arrows. Referring to FIG. 5, the radiation pattern or sensitivity pattern of an array of transmit elements 11 at a constant one-half wavelength spacing is characterized by a grating side lobe $T_s$ at a much greater angle from the main lobe $T_m$ than was the case for the one wavelength spacing. Transmitted ultrasonic energy generated by pulsing the elements in time sequence is in phase within the main beam and grating side lobe, and also the small diffraction side lobes, and cancels out at other places. The interelement spacing is D in the grating equation, $\lambda = D \sin \theta$, and the angle must increase as the interelement spacing decreases. For a spacing of one-half wavelength, the grating side lobe structure is so far away from the main beam as to be negligible. The same type of reasoning explains the discriminating characteristic of the receiver, in that coherent summation of the contributions of all active receiving channels effectively sums echo signals that are in phase, and echo signals out of phase cancel one another. The overall sensitivity pattern in FIG. 6 for the present transmit-receive transducer array with different interelement spacings has a receiver side lobe $R_s$ at an angle from the main beam such it would be objectionable, but the transmitter array pattern in that direction is very small and therefore the product of side lobe sensitivities is small.

Figure 7:
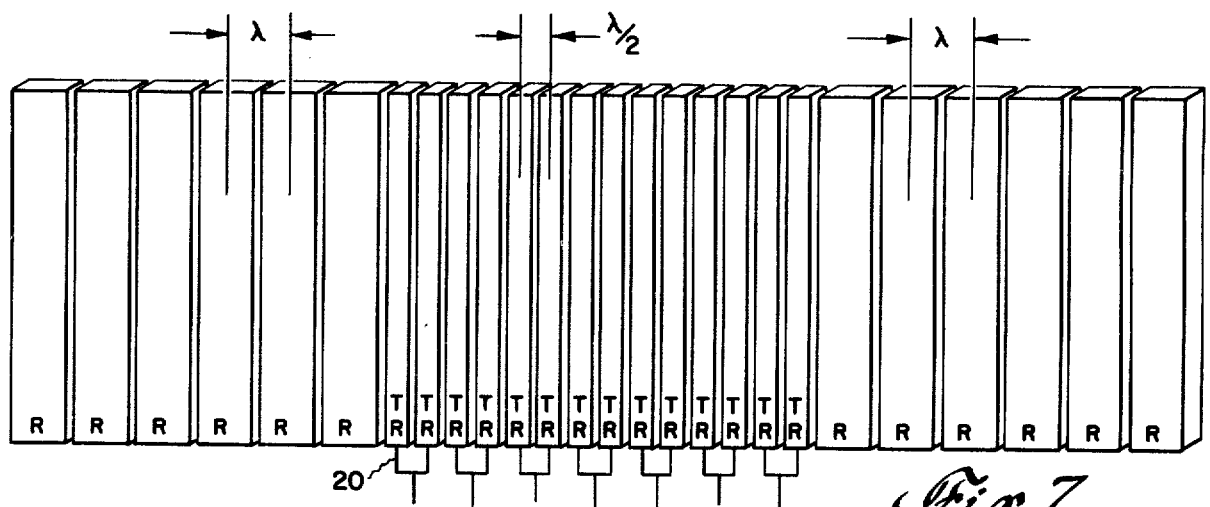
FIG. 7 is the preferred embodiment of the transmit-receive array and is 100 percent active.

The preferred embodiment of the transmit-receive transducer array in FIG. 7 is a 100 percent active transducer, is physically small, and has a single continuous row of elements comprised of a central sub-array of equally spaced transmit-receive (TR) elements between two end sub-arrays of equally spaced receive-only (R) elements. The interelement spacing of the receive-only elements is one wavelength and the spacing of the transmit-receive elements is one-half wavelength. The shorter transmitting sub-array has a constant spacing of one-half wavelength and every TR element is a unit transmit element connected to a separate transmitting channel and pulser. The longer receive array has a constant spacing of one wavelength, and for this purpose pairs of adjacent TR elements are coupled together electrically at 20 so that the individual received echo signals for each two TR elements are combined and processed through one receiving channel for the two elements. Every receive-only element R is a unit receive element connected to a separate receiving channel, and every group of connected-together TR elements is also a unit receive element.

The transducer array is conveniently fabricated from a single slab of piezoelectric material by making a series of identical saw cuts defining the individual elements. The array can be flat or can be curved along the longitudinal axis of the separate elements, or curved along the longitudinal axis of the total array, or both. One array suitable for medical diagnostic examination and cardiology in particular is made up of a central sub-array of 40 TR elements and end sub-arrays each with 17 R elements. There are then 40 transmit elements and transmitting channels, and 54 unit receive elements and receiving channels. At an ultrasonic frequency of 2.25 megahertz, one wavelength is 0.68 millimeters and at a frequency of 3.5 megahertz one wavelength is 0.44 millimeters. Thus, the elements are very small and the total length of the array in one case is 3.5 centimeters and in the other case 2.5 centimeters. It is essential for cardiology that the transducer probe be small and easily maneuvered by the physician because the heart is viewed from between the ribs or the probe is inserted under a rib and angled. Furthermore, vertical shots or images in vertical planes through the heart are often wanted. This transducer configuration is 100 percent active during every transmit-receive cycle.

Although the interelement spacing in the center portion of the array, between transmit-receive and transmit-only elements in FIG. 2 and between transmit-receive elements in FIG. 7, has been described as being one-half wavelength, it is also possible to use spacings of one-third wavelength, One-quarter wavelength, and so on. The center portion of the array must be a periodic structure and there are an integer number of TR and T elements, or TR elements, within one period referenced to the spacing of the unit receive elements. Stated conversely, the spacing of the receive-only elements in the array is an integer number of times greater than the spacing of the smaller elements in the center portion of the array.

Figure 8:
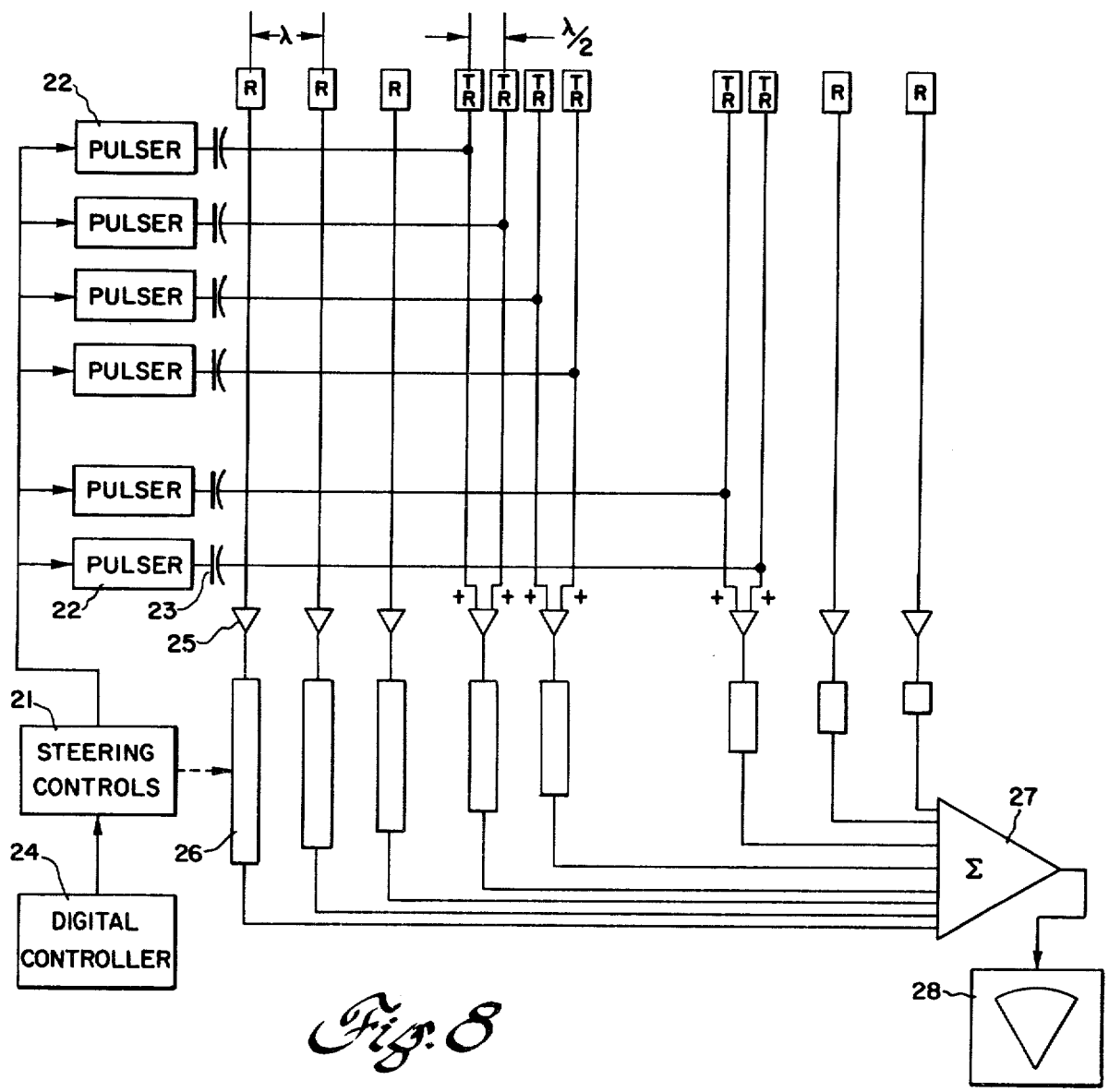
FIG. 8 is a simplified system block diagram of a steered beam ultrasonic imager constructed with the transducer array of FIG. 7.

FIG. 8 is a system block diagram of a single sector steered beam ultrasonic imaging system employing the transmit-receive transducer array configuration of FIG. 7 with one receiving channel connected to every two adjacent receive elements in the center portion of the array. The TR elements in the central sub-array spaced at one-half wavelength are connected to a like number of transmitting channels having the capability of producing element excitation pulses in time sequence to steer the generated angulated acoustic beams. Steering controls 21 contain adjustable delays and trigger transmit pulsers 22 in sequence to generate excitation pulses which are applied through capacitors 23 to the transmit elements. Digital controller 24 produces start pulses for controlling generation of the acoustic beams and operation of the imager as the sector scan is made. The parallel receiving channels for every receive-only element R and every connected-together pair of transmit-receive elements TR, each include a preamplifier 25 having a limiter to protect the sensitive preamplifier inputs from the high transmitting voltage, and an adjustable-delay element 26 such as a charge coupled device (CCD) delay line for time delaying the received echo electrical signal to focus the echoes. The steering delays are depicted as rectangular blocks which vary in length from channel to channel and have a magnitude determined by the steering delay control. The delayed echo signals from the parallel receiving channels are fed to a summing amplifier 27 to effect coherent summation of the contributions of all the receive elements, and the output is a focused echo signal or raw video data which may be post-processed to improve the picture quality before being fed to a cathode ray tube 28 or television monitor for visual display in real time. The combined echo signals from every pair of adjacent TR elements are processed through their receiving channels in the same manner as the received echo signals from a larger read-only element R.

The transmit-receive transducer array can also be utilized in the ultrasonic multi-sector scanner disclosed and claimed in an allowed copending application with that title, Ser. No. 825,528 filed Aug. 18, 1977 by H. A. F. Rocha and C. E. Thomas and assigned to the same assignee as this invention. This system has a longer linear transducer array for producing a set of sector scans with the origin points of the sequential sector scans displaced longitudinally along the array. Further information on specific circuitry and components for sector scanners for real time imaging is given in this application. In conclusion, the ability to reduce grating side lobe levels in wide aperture array steered beam imaging systems while maintaining low cost and complexity will lead to increased performance in medical applications and in the nondestructive testing of metal and ceramic parts.

While the invention has been particularly shown and described with reference to several preferred embodiments thereof, it will be understood by those skilled in the art that various changes in form and details may be made therein without departing from the spirit and scope of the invention.

What is claimed is:

1. A transmit-receive transducer array for steered beam ultrasonic imaging systems including a single row of electroacoustic transducer elements comprised of a shorter transmit array of equally spaced transmit elements that is approximately centered within a longer receive array of equally spaced unit receive elements, the spacing between said transmit elements being substantially less than the spacing between said unit receive elements so that the grating side lobe upon transmission is at a substantially greater angle from the main beam than is the grating side lobe upon reception and the product of side lobe sensitivities is small, the center portion of said row of transducer elements being comprised solely of transmit-receive elements and either end portion of said row being comprised of receive-only elements, said receive-only elements being unit receive elements, and means for electrically coupling together adjacent transmit-receive elements by groups during reception such that each group functions as a unit receive element.

2. The transducer array of claim 1 wherein the interelement spacing of said transmit-receive elements is one-half wavelength of the transmitted ultrasonic energy and the interelement spacing of said receive-only elements is one wavelength.

3. A transmit-receive transducer array for a steered beam ultrasonic imaging system including a single continuous row of electroacoustic transducer elements comprised of a central sub-array of equally spaced transmit-receive elements between two end sub-arrays of equally spaced receive-only elements, the interelement spacing of said receive-only elements further being an integer number of times greater than the interelement spacing of said transmit-receive elements, said transmit-receive elements being capable of individual excitation during transmission, and means for electrically coupling together plural adjacent transmit-receive elements by groups during reception such that the spacing between connected-together groups is the same as the interelement spacing between receive-only elements, whereby the grating side lobe during transmission is at a substantially greater angle from the main beam than is the grating side lobe upon reception and the product of side lobe sensitivities is small.

4. The transducer array of claim 3 wherein the interelement spacing of said transmit-receive elements is one-half wavelength of the transmitted ultrasonic energy and the interelement spacing of said receive-only elements is one wavelength.

5. A steered beam ultrasonic imaging system comprising
a transmit-receive transducer array having a single continuous row of transducer elements comprised of a central sub-array of equally spaced transmit-receive elements between two end sub-arrays of equally spaced receive-only elements, the interelement spacing of said receive-only elements being an integer number of times greater than the interelement spacing of said transmit-receive elements, and means for electrically coupling together plural adjacent transmit-receive elements by groups such that the spacing between connected-together groups is the same as the interelement spacing between receive-only elements, whereby the product of side lobe sensitivities is small,
a plurality of transmitting channels individually connected to each transmit-receive element and generating excitation pulses in time sequence,
a plurality of receiving channels individually connected to said receive-only elements and to said connected-together groups of transmit-receive elements for amplifying and time delaying received echo electrical signals, and
means for summing the delayed echo signals to thereby generate a focused echo signal and for displaying the focused echo signal as a visual image of the insonified object region.

6. The imaging system of claim 5 wherein the interelement spacing of said transmit-receive elements is one-half wavelength of the transmitted ultrasonic energy and the interelement spacing of said receive-only elements is one wavelength.

7. A transmit-receiver transducer array for steered beam ultrasonic imaging systems including a single row of electroacoustic transducer elements comprised of a shorter array of equally spaced transmit elements that is approximately centered within a longer array of equally spaced unit receive elements, the interelement spacing of said transmit elements being approximately half the interelement spacing of said unit receive elements so that the grating side lobe upon transmission is at a substantially greater anlge from the main beam than is the grating side lobe upon reception and the product of side lobe sensitivities is small, the center portion of said row of elements being solely transmit-receive elements and both end portions being solely receive-only elements.

8. The transducer array of claim 7 further including means for electrically connecting together selected pairs of adjacent elements during reception such that connected-together elements form a unit receive element.

9. A transmit-receive transducer array for steered beam ultrasonic imaging systems including a single row of electroacoustic transducer elements comprised of a shorter transmit array of equally spaced transmit elements that is approximately centered within a longer receive array of equally spaced unit receive elements, the interelement spacing of said unit receive elements being an integer number of times greater than the interelement spacing of said transmit elements so that the grating side lobe upon transmission is at a substantially greater angle from the main beam than is the grating side lobe upon reception and the product of side lobe sensitivities is small, the center portion of said row of transducer elements being solely transmit-receive elements and both end portions of said row being solely receive-only elements, said transmit-receive elements being capable of individual excitation during transmission, and means for electrically coupling together at least adjacent transmit-receive elements by groups during reception such that each group functions as a unit receive element.

10. A steered beam ultrasonic imaging system comprising:
   a transmit-receive transducer array having a single continuous row of transducer elements comprised of a shorter transmit array of equally spaced transmit elements that is approximately centered within a longer receive array of equally spaced unit receive elements, the interelement spacing of said unit receive elements being approximately twice the interelement spacing of said transmit elements so that the product of grating side lobe sensitivities is small, the center portion of said row of elements being transmit-receive elements and both end portions being receive-only elements, and means for electrically coupling at least adjacent pairs of transmit-receive elements during reception,
   a plurality of transmitting channels individually connected to each transmit-receive element and generating excitation pulses in time sequence,
   a plurality of receiving channels, one per unit receive element, connected to said transmit-receive and receive-only elements for amplifying and time delaying received echo electrical signals, and
   means for summing the delayed echo signals to thereby generate a focused echo signal and for displaying the focused echo signal as a visual image of the insonified object region.

* * * * *